United States Patent
Zhang et al.

(10) Patent No.: US 8,889,585 B2
(45) Date of Patent: Nov. 18, 2014

(54) MESOPOROUS CARBON SUPPORTED TUNGSTEN CARBIDE CATALYSTS, PREPARATION AND APPLICATIONS THEREOF

(75) Inventors: Tao Zhang, Dalian (CN); Yanhua Zhang, Dalian (CN); Aiqin Wang, Dalian (CN); Mingyuan Zheng, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 303 days.

(21) Appl. No.: 13/395,460

(22) PCT Filed: Oct. 22, 2010

(86) PCT No.: PCT/CN2010/077981
§ 371 (c)(1),
(2), (4) Date: Mar. 12, 2012

(87) PCT Pub. No.: WO2011/050691
PCT Pub. Date: May 5, 2011

(65) Prior Publication Data
US 2012/0178974 A1    Jul. 12, 2012

(30) Foreign Application Priority Data
Oct. 27, 2009    (CN) .......................... 2009 1 0188221

(51) Int. Cl.
| | |
|---|---|
| *B01J 21/18* | (2006.01) |
| *B01J 23/00* | (2006.01) |
| *C07C 27/00* | (2006.01) |
| *C07C 29/00* | (2006.01) |
| *C07C 31/18* | (2006.01) |
| *B01J 27/22* | (2006.01) |
| *B01J 35/10* | (2006.01) |
| *B01J 37/00* | (2006.01) |
| *B01J 37/02* | (2006.01) |
| *B01J 37/08* | (2006.01) |

(52) U.S. Cl.
CPC ... *B01J 27/22* (2013.01); *B01J 21/18* (2013.01); *B01J 35/1061* (2013.01); *B01J 37/0018* (2013.01); *B01J 37/0201* (2013.01); *B01J 37/084* (2013.01); *C07C 29/00* (2013.01); *B01J 35/1028* (2013.01); *B01J 35/1047* (2013.01)
USPC ........................................... 502/182; 568/861

(58) Field of Classification Search
USPC ........................................... 502/182; 568/861
See application file for complete search history.

(56) References Cited

U.S. PATENT DOCUMENTS

| | | |
|---|---|---|
| 3,684,579 A | 8/1972 | Mund et al. |
| 4,155,928 A | 5/1979 | Finch |

(Continued)

FOREIGN PATENT DOCUMENTS

| | | | | |
|---|---|---|---|---|
| CN | 101117222 A | | 2/2008 | |
| CN | 101411975 | * | 4/2009 | ............... B01J 23/30 |

(Continued)

OTHER PUBLICATIONS

"Synthesis of New, Nanoporous Carbon with Hexagonally Ordered Mesostructure," Shinae Jun et al. J. Am. Chem. Soc. 2000, 122, pp. 10712-10713.*

(Continued)

*Primary Examiner* — Patricia L Hailey
(74) *Attorney, Agent, or Firm* — Novick, Kim & Lee, PLLC; Allen Xue

(57) ABSTRACT

A supported tungsten carbide catalyst comprises tungsten carbide as its active component and a mesoporous carbon as its support, wherein tungsten carbide is highly dispersed on the surface and in the channels of the mesoporous carbon, and the content of tungsten element is in the range from 30% to 42% by mass based on the mesoporous carbon. This catalyst can be prepared by impregnation process. This catalyst can be used for the direct catalytic conversion of cellulose to ethylene glycol under the hydrothermal conditions and at a temperature of 245° C. and the hydrogen pressure of 6 MPa with high reactivity, selectivity and stability.

13 Claims, 2 Drawing Sheets

(56) References Cited

U.S. PATENT DOCUMENTS

| | | | |
|---|---|---|---|
| 6,297,185 B1 | 10/2001 | Thompson et al. | |
| 7,196,122 B2 * | 3/2007 | Ryoo et al. | 523/218 |
| 7,767,867 B2 | 8/2010 | Cortright | |
| 7,910,082 B2 * | 3/2011 | Dawes et al. | 423/346 |
| 7,960,594 B2 * | 6/2011 | Zhang et al. | 568/861 |
| 8,222,462 B2 * | 7/2012 | Kalnes et al. | 568/852 |
| 8,222,463 B2 | 7/2012 | Kalnes et al. | |
| 8,222,464 B2 | 7/2012 | Kalnes et al. | |
| 8,222,465 B2 | 7/2012 | Kalnes et al. | |
| 8,323,937 B2 * | 12/2012 | Zhang et al. | 435/158 |
| 8,324,433 B2 | 12/2012 | Zhang et al. | |
| 8,338,326 B2 * | 12/2012 | Zhang | 502/177 |
| 8,410,319 B2 * | 4/2013 | Kalnes et al. | 568/861 |
| 8,563,124 B2 * | 10/2013 | Chmelka et al. | 428/304.4 |
| 2002/0198101 A1 | 12/2002 | Gaffney | |
| 2003/0077460 A1 | 4/2003 | Christian et al. | |
| 2007/0269707 A1 | 11/2007 | Lee et al. | |
| 2010/0040834 A1 * | 2/2010 | Dawes et al. | 428/158 |
| 2010/0256424 A1 | 10/2010 | Zhang et al. | |
| 2011/0312051 A1 | 12/2011 | Kalnes et al. | |
| 2011/0312487 A1 | 12/2011 | Chen et al. | |

FOREIGN PATENT DOCUMENTS

| | | | |
|---|---|---|---|
| CN | 101411975 A | 4/2009 | |
| CN | 101428213 A | 5/2009 | |
| CN | 101648140 * | 2/2010 | B01J 27/22 |
| CN | 101648140 A | 2/2010 | |
| CN | 101869853 A | 10/2010 | |
| CN | 102049273 A | 5/2011 | |
| WO | 02/28544 A1 | 4/2002 | |
| WO | 2010/017681 * | 2/2010 | C07C 31/20 |

OTHER PUBLICATIONS

Na Ji, et al. "Catalytic Conversion of Cellulose into Ethylene Glycol Over Supported Carbide Catalysts." Catalysis Today, vol. 147 (2009), pp. 77-85.

* cited by examiner

MESOPOROUS CARBON SUPPORTED TUNGSTEN CARBIDE CATALYSTS, PREPARATION AND APPLICATIONS THEREOF

BACKGROUND OF THE INVENTION

1. Field of the Invention

The invention relates to catalysts for direct catalytic conversion of cellulose into ethylene glycol, and more particularly to mesoporous carbon supported tungsten carbide catalysts and preparation and applications thereof.

2. Background

Energy is the base of modern society survival and development. The exploitation and utilization of clean energy affects the sustainable development of national economy, and it's the basic guarantee for the national security strategy.

Biomass represents a promising renewable resource. Its utilization and development plays an important role in keeping energy diversity, reducing dependence on fossil oil, and maintaining energy security. Cellulose is the most abundant second generation of biomass resources. It is readily available and inexpensive, e.g., from agricultural wastes and forestry wastes. Meanwhile, cellulose is non-edible and is not a threat to the food security of human being. Therefore, how to convert cellulose into value-added products is a hot research topic among scholars of many nations.

Conventional methods for cellulose conversion focus on hydrolysis in mineral acids or through enzymatic degradation. These methods are of low efficiency and high pollution, therefore facing serious challenges. In comparison, catalytic conversion of cellulose developed in recent years is a highly efficient, green method. The catalytic conversion of cellulose is to degrade cellulose into polyhydroxy compounds in the presence of a catalyst under certain conditions. Professor Fukuoka in Japan used $Pt/Al_2O_3$ as the catalyst and obtained 30% yield of hexitols. Employing a Ru/AC catalyst, Professor H. C. Liu of Peking University further improved the hexitol yield to 40% (CN101058531). Professor Y. Wang of Xiamen University achieved a hexitol yield above 50% by pre-treating cellulose in phosphoric acid, regenerating the precipitants using water, and then using a Ru catalyst supported on multiwall carbon nanotubes (MWCNT) in catalytic hydrogenation conversion of cellulose (CN101121643). However, since noble metals were employed in above cases, these methods are of high cost and low economic efficiency.

Recently, we developed a nickel promoted tungsten carbide catalyst loaded on AC for catalytic conversion of cellulose into ethylene glycol under hydrothermal conditions. The reaction is highly efficient with good selectivity, giving the ethylene glycol yield as high as 61%. However, the nickel addition on the catalyst accelerated the tungsten carbide aggregation. Furthermore, the micro structure of AC decreased the dispersion of tungsten carbide on the catalyst and limited the diffusion of reactants and products.

The mesoporous carbon has a relatively high surface area, a large pore volume, is high in acid and alkali resistance and highly hydrothermal stability. Therefore, it is widely used in fuel cell, sensor, adsorption separation, catalysis, and etc.

It is known that the activity and selectivity of a catalyst relates the dispersion of active component and the diffusion of reactants to active sites. Mesoporous carbon supported catalysts promote the dispersion of active metals, increase accessibility of the pores, contribute to molecular diffusion, and consequently increase the activity and selectivity of catalysts. There is no report regarding the application of mesoporous carbon supported tungsten carbide on catalytic conversion of cellulose to ethylene glycol up to now.

SUMMARY OF THE INVENTION

It is an objective of the invention to provide methods for preparing mesoporous carbon supported catalysts and their applications. The catalysts can catalytically convert cellulose into ethylene glycol under hydrothermal conditions with high yield and selectivity.

To achieve the objective described above, in accordance with one embodiment of the invention, there is provided a catalyst comprising tungsten carbide loaded on three-dimensional (3D) interconnected amorphous mesoporous carbon MC, MC—R, denoted as WCx/MC (x=0.5-1) and WCx/MC—R(x=0.5-1), and a catalyst comprising tungsten carbide loaded on ordered mesoporous carbon CMK-3, CMK-8, denoted as WCx/CMK-3 (x=0.5-1) and WCx/CMK-8 (x=0.5-1). The supports for the catalysts are respectively the three-dimensional (3D) interconnected amorphous mesoporous carbon MC, MC—R and ordered mesoporous carbon CMK-3, CMK-8. The active component of catalysts is WCx (x=0.5-1). When nickel is added, the active component of catalysts is Ni—WCx (x=0.5-1), in which the metal component W accounts for between 1 and 80 wt % of the catalyst, preferably between 30 and 42 wt %; the metal component of Ni accounts for between 0.1 and 30 wt % of the catalyst, and preferably between 2 and 5 wt %.

Above described carbon supports MC, CMK-3 and CMK-8 are synthesized using nanocasting method. In particular, 1.0 g of hard template was impregnated with 0.1-10 g of sucrose in a solution containing 0.1-0.3 g of concentrated $H_2SO_4$ and 5-8 mL of $H_2O$. The resultant mixture was heated at 40-350° C. for not less than 0.5 hour, and preferably heated at 95-110° C. and 160-170° C. for 6-8 hrs respectively. The final solid was carbonized at 400-1000° C. in inert atmosphere, e.g., $N_2$, for not less than 0.5 hour, and preferably carbonized at 800-900° C. for 3-6 hrs. Finally, the hard template was removed in a HF or NaOH solution. The concentration of acid or alkali is properly selected for removing the template without disrupting the structure of channels. After washing in deionized water, the material is placed in an oven to be dried drying at 60-120° C., three-dimensional (3D) interconnected amorphous MC and ordered CMK-3, CMK-8 were obtained.

The above-described catalyst support MC—R is synthesized by nanocasting method. Commercially available silica sol with 5-100 nm diameter is used as the hard template. The carbon source is the sol of resorcinol (R) and formaldehyde (F) with R/F mole ratio is 0.1-2. Stirring the mixture R and F and silica sol, wherein the Si/R mole ratio is 0.1-20, for not less than 10 minutes. The mixture was then heated at 40-160° C. for not less than 0.5 hour. The final solid was carbonized at 400-1000° C. in a reducing atmosphere for not less than 0.5 hour. Finally the hard template was removed using a HF or NaOH solution. The concentration of acid or alkali is properly selected for removing the template without disrupting the structure of channels. After washing in deionized water, the material was dried at 60-120° C. to obtain a mesoporous carbon called MC—R.

The catalyst is prepared by impregnating active component salt solution on the support. In particular, soluble salts of the active components in the catalyst are weighed according to their ratio and dissolved in deionized water to obtain a solvent. Mesoporous carbon support is impregnated with this solvent. The precursor impregnated with active component is dried at 40-160° C. and carburized in a $H_2$ flow for not less than 1 hour. The catalyst without Ni is carburized at 850-1000° C. while the catalyst with Ni is carburized at 650-800° C.

The catalysts described above can be used in the catalytic hydrogenation degradation of cellulose. The reaction is conducted in a sealed high-pressure reactor with stirring. The weight ratio of the cellulose to water is between 1:200 and 1:1. The weight ratio of the cellulose to the catalyst is between 1:1 and 100:1. The initial hydrogen pressure therein at room temperature being between 1 and 12 MPa. The reaction temperature increases in a controlled manner to 120-300° C., and the reaction time being not less than 10 min.

The catalyst of current invention uses high surface area, large pore volume mesoporous carbon as the support, which enhances the dispersion of active components, and the diffusion of reactant and products moleculars, which increases the activity and selectivity of catalysts. The catalyst can convert cellulose into ethylene glycol with high yield and high selectivity in hydrogen under hydrothermal conditions. The raw material for the catalyst of the current invention is readily available. The preparation is simple. It has great prospect.

Compared with recently reported tungsten carbide catalysts, the mesoporous carbon supported tungsten carbide catalyst has better activity, selectivity and stability.

DETAILED DESCRIPTION OF THE EMBODIMENTS

Example 1

Figure 1:
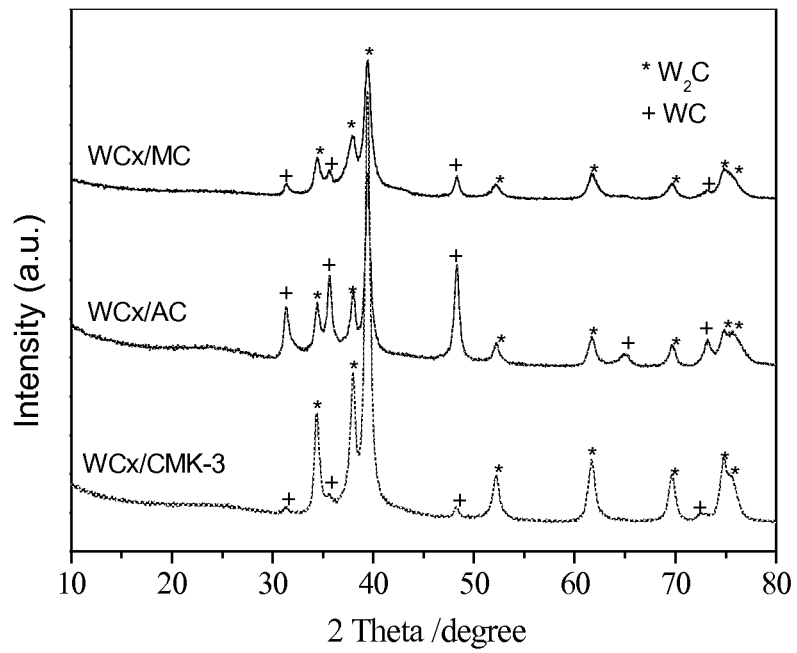
FIG. 1 shows the results of X-ray powder diffraction analysis of catalyst in Examples 3, 4 and Comparative Example 1.

Preparation of MC and CMK-3 Support with Hard Template Method 1.0 g of commercially available silica or SBA-15 was impregnated in a solution containing 1.25 g of sucrose and 0.14 g of concentrated $H_2SO_4$ in 5 ml $H_2O$. The resultant mixture was placed at ambient temperature for 8-12 hrs (12 hrs in this example), dried first at 100° C. for 6 hrs and then at 170° C. for 6 hrs. The powdery substance obtained was once again impregnated in a solution containing 0.8 g of sucrose and 0.09 g of concentrated sulfuric acid in 5 ml $H_2O$, followed by the same heating steps as described above. The sample obtained after the heating steps was carbonized at 900° C. in $N_2$ for 6 hrs and then cooled to room temperature. The sample thus obtained was placed in 5 wt % HF or 2 M NaOH solution at 60-80° C. for 2-24 hrs (24 hrs in this example) to remove the silica template. After filtration, washing, and drying at 80-120° C. (120° C. in this example), MC or CMK-3 was obtained. The parameters for pore structure of the as-prepared carbon supports are compared with that of the active carbon AC in comparative example 1 and the results are shown in Table 1.

TABLE 1

The pore structure of different carbon supports

| Support | $S_{BET}$ (m$^2$/g) | $S_{micro}$ (m$^2$/g) | $V_{micro}$ (cm$^3$/g) | $V_{meso}$ (cm$^3$/g) | Dp (nm) |
|---------|---------------------|------------------------|-------------------------|------------------------|---------|
| MC      | 1124                | 288                    | 0.13                    | 1.28                   | 4.9     |
| CMK-3   | 1376                | 91                     | 0.03                    | 1.60                   | 3.7     |
| AC      | 1102                | 748                    | 0.34                    | —                      | —       |

As shown in Table 1, the surface areas of all three carbon supports are similar. However, the surface area of MC and CMK-3 is attributable to the mesopores, while the surface area of AC is attributable to micro pores. In addition, the mesoporous carbon has a relatively large volume of mesopores and a relatively narrow pore distribution. The average pore size of the MC is 4.9 nm, and the average pore size of the CMK-3 is 3.7 nm.

Example 2

Preparation of Mesoporous Carbon MC—R with Hard Template Method

A mixed solution of 5.5 g of resorcinol (R) and 8.5 g of formaldehyde (F) was prepared. 30 g of 40 wt % silica sol (Ludox HS-40y) was mixed with the as-prepared RF sol. The resultant mixture was first treated at 50° C. for 24 hrs and then treated at 90° C. for 72 hrs, and then was carbonized at 900° C. in $N_2$ for 3 hrs. Finally the silica was washed out using HF. After drying at 80° C. overnight, MC—Rm were obtained (m represents the molar ratio of Si to R). The pore structure parameters of MC—R supports with different Si/R are shown in Table 2.

TABLE 2

The pore structure of MC-R supports with different Si/R ratios

| | $S_{BET}$ (m$^2$/g) | $S_{micro}$ (m$^2$/g) | $V_{micro}$ (cm$^3$/g) | $V_{meso}$ (cm$^3$/g) | D (nm) |
|---|---|---|---|---|---|
| MC-R4 | 1022 | 196 | 0.08 | 2.36 | 9.6 |
| MC-R2 | 621  | 203 | 0.09 | 1.02 | 8.7 |
| MC-R1 | 514  | 246 | 0.11 | 0.53 | 8.1 |

Example 3

Preparation of a WCx/MC (x=0.5-1) Catalyst Using Impregnation 1.0 g of mesoporous carbon MC was impregnated with an aqueous solution containing 0.588 g of ammonium metatungstate (AMT) in 3-4 ml $H_2O$, followed by drying at 120° C. in an oven. The sample was then reduced in an $H_2$ flow of 120 ml/min under controlled heating: from room temperature to 550° C. at 8.8° C./min, and then to 900° C. at 1° C./min and held at that temperature for 1 h. The theoretical loading of W in the catalyst was 30 wt %.

Example 4

Preparation of a WCx/CMK-3 (x=0.5-1) Catalyst Using Impregnation

The preparation method was the same as described in Example 3, except that the carbon support was CMK-3 prepared in Example 1. The theoretical loading of W in the catalyst was 30 wt %.

Example 5

Preparation of WCx/MC-60 wt % and WCx/CMK-8-10 wt % (x=0.5-1) Catalysts Using Impregnation The preparation method was the same as in Example 3, except that the theoretical loadings of W in the catalyst were 60 wt % and 10 wt % respectively.

Example 6

Preparation of a WCx/MC—Rm Catalyst Using Impregnation

The preparation method was the same as in Example 3, except that the carbon support was MC—R prepared in Example 2. The theoretical loading of W in the catalyst was 30 wt %.

Comparative Example 1

Preparation of WCx/AC (x=0.5-1) Using Impregnation

The preparation method was the same as in Example 3, except that the carbon support was common active carbon AC having a similar surface area as MC. The theoretical loading of W in the catalyst was 30 wt %.

Figure 2:
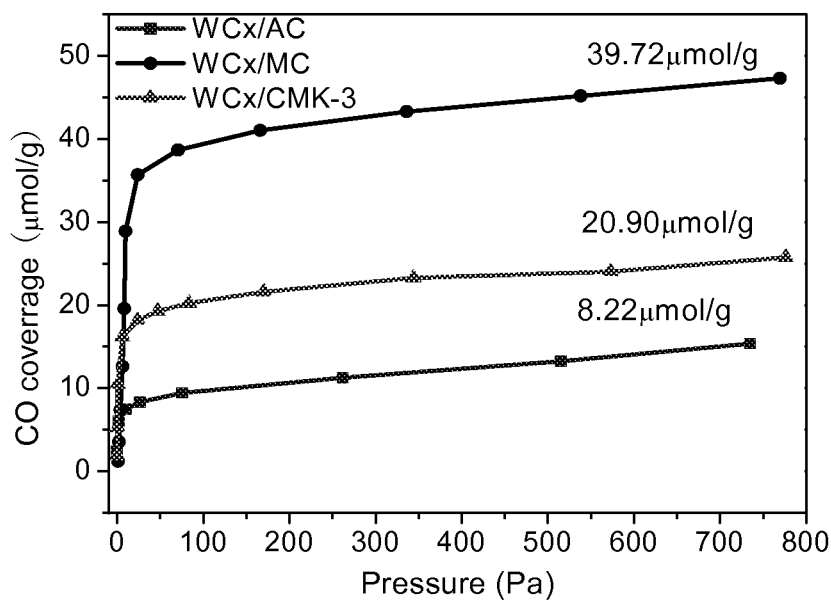
FIG. 2 shows the results of CO chemsorption analysis of catalyst in Examples 3, 4 and Comparison Example 1.

As shown in the XRD diffraction patterns in FIG. 1, the strongest peaks for tungsten carbide on MC support—WCx/MC— obviously are broader than those of tungsten carbide supported on other two carbon supports, indicating a smaller average particle size of the tungsten carbide on the MC support. As shown in FIG. 2, the CO chemsorption on WCx/MC, WCx/CMK-3 and WCx/AC catalyst are 39.72, 20.90 and 8.22 μmol/g respectively, which suggests that the tungsten carbide particles are better dispersed on three-dimensional (3D) interconnected mesoporous carbon (MC) support.

Comparative Example 2

Preparation of Ni—WCx/MC, Ni—WCx/CMK-3 and Ni—WCx/AC Catalysts Using Co-Impregnation 1.0 g of the carbon support was impregnated with an aqueous solution containing 0.588 g ammonium metatungstate (AMT) and 0.157 g nickel nitrate in 3-4 ml $H_2O$, followed by drying at 120° C. in an oven. The catalyst precursor was then carburized in an $H_2$ flow of 60 ml/min under controlled heating: from room temperature to 450° C. at 8.8° C./min, and then to 750° C. at 1° C./min and holding at that temperature for 1 h. The theoretical loadings of W and Ni in the catalyst were 30 wt % and 2 wt % respectively.

Figure 3:
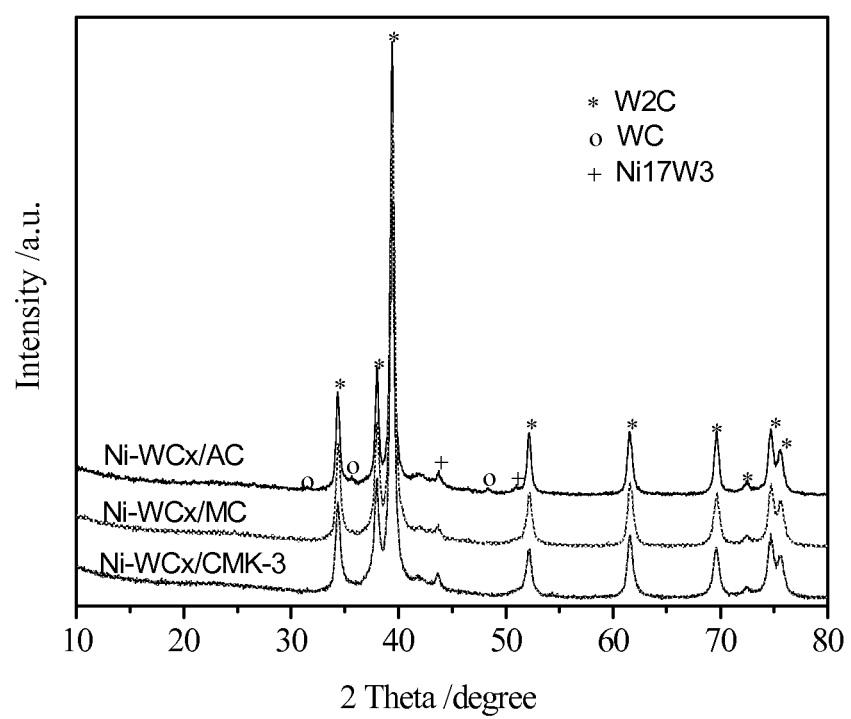
FIG. 3 shows the results of X-ray powder diffraction analysis of different catalysts in Example 2.

As shown in FIG. 3, the XRD diffraction peaks of tungsten carbide on the nickel prompted catalysts are sharper than those without Ni addition, indicating that the addition of Ni promoted the aggregation of tungsten carbide particles.

Example 7

Experiments of Catalytic Degradation of Cellulose 1.0 g of cellulose, 0.3 g of catalyst prepared as described above, and 100 mL water were charged in a 300 mL reactor. The reactor was filled with hydrogen and vented six times to remove air. Subsequently, hydrogen pressure in the reactor was increased to 6 MPa. The mixture was stirred at 1000 rpm. Meanwhile, the temperature therein was raised to 245° C. After reacting for thirty minutes, the mixture in the reactor was cooled to room temperature and filtered to yield a supernatant. The supernatant was analyzed using high performance liquid chromatography (HPLC) with a calcium ion-exchange column and detected using a refractive index detector. Cellulose conversions were determined by the change in the weight of dry solid before and after the reaction. The yield of liquid products was calculated according to the equation: yield (%)= (weight of the product)/(weight of cellulose)×100%.

TABLE 3

Catalytic conversion of cellulose in the presence of various catalysts

| Catalyst | Conversion (%) | Yield (%) | | | | |
|---|---|---|---|---|---|---|
| | | EG | Sor. | Man. | Ery. | PG |
| WCx/MC | 100 | 72.9 | 1.2 | 1.4 | 1.5 | 5.1 |
| WCx/CMK-3 | 100 | 71.1 | 1.7 | 2.4 | 1.9 | 6.4 |
| WCx/CMK-8-10 wt % | 100 | 54.1 | 1.0 | 2.2 | 1.5 | 5.2 |
| WCx/AC | 100 | 47.5 | 0.6 | 1.1 | 1.1 | 3.6 |
| WCx/MC-60 wt % | 100 | 70.2 | 1.8 | 1.6 | 1.9 | 4.8 |
| WCx/MC-R4 | 100 | 52.4 | 0 | 0.6 | 1.2 | 6.2 |
| WCx/MC-R2 | 100 | 53.1 | 1.1 | 1.3 | 1.6 | 6.7 |
| WCx/MC-R1 | 99.5 | 57.9 | 2.3 | 1.4 | 1.3 | 4.9 |
| Ni-WCx/MC | 100 | 74.4 | 2.2 | 3.0 | 2.3 | 4.5 |
| Ni-WCx/CMK | 100 | 72.4 | 1.5 | 2.5 | 1.5 | 5.3 |
| Ni-WCx/AC | 100 | 61.7 | 5.4 | 3.9 | 4.2 | 3.4 |

Note:
EG, Sor., Man., Ery. and PG represent Ethylene glycol, Sorbitol, Mannitol, Erythritol and 1,2-propylene glycol, respectively. Beside the noted loading percent in Table 3, the loadings of W and Ni catalysts are 30 wt % and 2 wt %.

As shown in Table 3, using various mesoporous carbon supported tungsten carbide catalysts in this invention, cellulose was degraded into ethylene glycol with high activity and selectivity even without nickel as the promoter. The yield of ethylene glycol surpassed 70%. The high activity of mesoporous carbon supported catalysts may lies in the mesoporous structure of MC support which enhances the dispersion of tungsten carbide and transportation of reactant and product molecules, thus leading to a significantly better selectivity. The addition of nickel increased the yield of ethylene glycol. On the other hand, for the mesoporous carbon supported catalysts, the addition of nickel caused the aggregation of tungsten carbide particles. Consequently, the increase in the yield of ethylene glycol was not obvious.

What is claimed is:
1. A mesoporous carbon supported tungsten carbide catalyst, comprising:
a mesoporous carbon support;
tungsten carbide dispersed on the mesoporous carbon support,
wherein tungsten accounts for 1 wt % to 80 wt % of the weight of the mesoporous carbon supported tungsten carbide catalyst.
2. The mesoporous carbon supported tungsten carbide catalyst of claim 1, further comprising nickel, wherein nickel accounts for 0.1 wt % to 30 wt % of the mesoporous carbon supported tungsten carbide catalyst.
3. The mesoporous carbon supported tungsten carbide catalyst of claim 2, wherein nickel accounts for 2 wt % to 5 wt % of the weight of the mesoporous carbon supported tungsten carbide catalyst.
4. The mesoporous carbon supported tungsten carbide catalyst of claim 1, wherein the mesoporous carbon support is chosen from an amorphous mesoporous carbon MC, an amor- phous mesoporous carbon MC—R, an ordered mesoporous carbon CMK-3, an ordered mesoporous carbon CMK-8, or mixtures thereof.

5. The mesoporous carbon supported tungsten carbide catalyst of claim 1, wherein tungsten accounts for 30 wt % to 42 wt % of the weight of the mesoporous carbon supported tungsten carbide catalyst.

6. The mesoporous carbon supported tungsten carbide catalyst of claim 1, wherein the mesoporous carbon support has a BET surface of higher than 1000 m$^2$/g.

7. A method for preparing a mesoporous carbon supported tungsten carbide catalyst of claim 1, comprising the steps of:
preparing a mesoporous carbon support;
impregnating the mesoporous carbon support with a solution comprising tungsten;
drying the impregnated mesoporous carbon support; and
carburized the dried impregnated mesoporous carbon support in a H$_2$ flow for more than 0.5 hour.

8. The method of claim 7, wherein the mesoporous carbon support is chosen from MC, CMK-3, CMK-8, or MC—R.

9. The method of claim 7, wherein the step of carburization is carried out at a temperature ranging from 850° C.-1000° C.

10. The method of claim 7, wherein the solution further comprises nickel and the step of carburization is carried out at a temperature ranging from 650° C.-800° C.

11. The method of catalytic conversion of cellulose, comprising:
obtaining a mesoporous carbon supported tungsten carbide catalyst of claim 1;
preparing a mixture comprising cellulose, water, and the mesoporous carbon supported tungsten carbide catalyst, wherein a weight ratio between cellulose and water ranges from 1:200 to 1:1 and a weight ratio between cellulose and the catalyst ranges from 1:1 to 100:1; and
heating the mixture to a temperature between 120° C. to 300° C. in an hydrogen atmosphere for more than 10 minutes.

12. The method of claim 11, wherein the weight ratio between cellulose and water is 1:100 and the weight ratio between cellulose and the catalyst ranges from 10:3.

13. The method of claim 11, wherein cellulose is converted to form ethylene glycol and a yield of ethylene glycol is higher than 70%.

* * * * *